(12) United States Patent
Bergin et al.

(10) Patent No.: US 8,679,131 B2
(45) Date of Patent: Mar. 25, 2014

(54) BONE PREPARATION REFERENCE GUIDE (75) Inventors: Alisha W. Bergin, Southaven, MS (US); Jerry J. Jones, Memphis, TN (US); Richard D. Lambert, Germantown, TN (US)

(73) Assignee: Smith & Nephew, Inc., Memphis, TN (US)

( * ) Notice: Subject to any disclaimer, the term of this patent is extended or adjusted under 35 U.S.C. 154(b) by 791 days.

(21) Appl. No.: 12/889,982

(22) Filed: Sep. 24, 2010

(65) Prior Publication Data
US 2011/0077658 A1 Mar. 31, 2011

Related U.S. Application Data (60) Provisional application No. 61/246,055, filed on Sep. 25, 2009.

(51) Int. Cl.
*A61B 17/58* (2006.01)
*A61B 17/60* (2006.01)
*A61F 2/00* (2006.01)

(52) U.S. Cl.
USPC ........................................................ 606/102

(58) Field of Classification Search
USPC ........................................................ 606/102
See application file for complete search history.

(56) References Cited

U.S. PATENT DOCUMENTS 5,607,431 A * 3/1997 Dudasik et al. ................. 606/80

OTHER PUBLICATIONS

Bourne, et al., "Leg Length/Offset Measurement Instrument" Smith & Nephew Orthopaedics Performance Innovation Trust, pp. 1-6 (2000).
Smith & Nephew Spectron EF Hip System Surgical Technique 12/14 Taper, pp. 1-25 and front and rear covers (1999).
Smith & Nephew ACCORD Cable System Surgical Technique Innovations in Hip Surgery, pp. 1-15 (2008).
Smith & Nephew First Choice in Orthopaedics SYNERGY™ Tapered Hip System, pp. 27 (1999).

* cited by examiner

*Primary Examiner* — Sameh Boles
(74) *Attorney, Agent, or Firm* — Krieg DeVault LLP (57) ABSTRACT A reference guide comprising an attachment portion configured to abut with and attach to an anatomical feature such as a bone. The reference guide further comprises a reference indicator that may be formed integrally with, or selectively securable to, the attachment portion and that indicates a reference point with respect to the attachment portion. The reference guide may be used to identify a target location during a surgical procedure even in the absence of traditional landmarks.

29 Claims, 6 Drawing Sheets

BONE PREPARATION REFERENCE GUIDE

CROSS-REFERENCE TO RELATED APPLICATIONS

This patent application claims the benefit of U.S. Provisional Application No. 61/246,055, filed Sep. 25, 2009, which is incorporated herein by reference in its entirety.

FIELD OF THE INVENTION

The present invention relates to bone preparation guides and methods for their use.

BACKGROUND OF THE INVENTION

During surgical procedures, and especially during revision procedures involving removal and replacement of a prosthetic component, important bony landmarks may be damaged or lost. For example, during a hip surgery, femoral landmarks such as the greater trochanter, lesser trochanter, femoral head center, and marks from previous implants may be lost or compromised due to pre-operative trauma or due to trauma when removing previous implant components. If needed landmarks are not available, a surgeon may not be able to accurately complete a surgical procedure. For example, without a guiding landmark, the surgeon may not be able to accurately determine a proper reaming or broaching depth.

Some techniques may attempt to rely on preoperative planning to identify alternative landmarks if it is known ahead of time that typical landmarks are compromised. However, this depends on knowing pre-operatively that the traditional landmarks are unavailable and requires that other suitable landmarks can be identified. In other techniques, a cautery pen or skin marker may be used to create a reference point for a procedure such as a bone preparation for placement of a replacement prosthetic component. Still another technique is to simply estimate distances or locations. For example, a surgeon may simply estimate a proper reamer depth. All of these methods have various drawbacks including a lack of accuracy or dependency on known and favorable surgical conditions.

Other known devices may provide length or offset guides, and may utilize, for example, a fixed pin and a predetermined mark on an anatomical landmark as a reference point for measuring leg length or offset intraoperatively. However, such devices may not be configured to attach in close proximity to an unprepared bone surface or to provide a guide for bone preparation. Other devices may provide a guide for resecting a portion of a bone for example, but can be dependent on certain anatomical structures being present in order to properly guide a resection and often such devices can only be used on a prepared bone surface and may not be able to attach on or in close proximity to the an unprepared bone surface.

SUMMARY

Embodiments of the present invention provide reference guides for use in surgical procedures and methods of their use. In one embodiment, a reference guide comprises a bone attachment portion and a reference indicator. The bone attachment portion comprises a bone abutment surface that can be configured to conform to the surface of an anatomical feature such as a bone and be secured thereto through an attachment aid such as cerclage cable. The reference guide may be formed integral with the attachment portion or may be a separate piece that is selectively securable to the attachment portion, permitting its removal during a surgical procedure.

Other embodiments provide a method of using a reference guide during surgery wherein a target location is determined, the position of the target location with respect to a reference guide is identified, and the reference guide is then used to identify the target location during a subsequent surgical procedure. According to certain embodiments, a reference indicator portion of the reference guide may be removed prior to performing a portion of the procedure and then replaced in order to identify the target location. For example, a desired position for a revision implant component may be identified with respect to the reference guide, the reference indicator may be removed in order to facilitate removal of an existing implant component and then re-secured after the existing component is removed. Because removal of the existing component may damage certain landmarks, the reference guide can be used to again locate the desire location for the revision implant component.

These and other embodiments are presented in greater detail in the detailed description which follows.

DETAILED DESCRIPTION

Embodiments of the present invention can be understood more readily by reference to the following detailed description, examples, and drawings and their previous and following descriptions. However, apparatus and methods of the present invention are not limited to the specific embodiments presented in the detailed description, examples, and drawings. It should be recognized that these embodiments are merely illustrative of the principles of the present invention. Numerous modifications and adaptations thereof will be readily apparent to those of skill in the art without departing from the spirit and scope of the invention.

Figure 1:
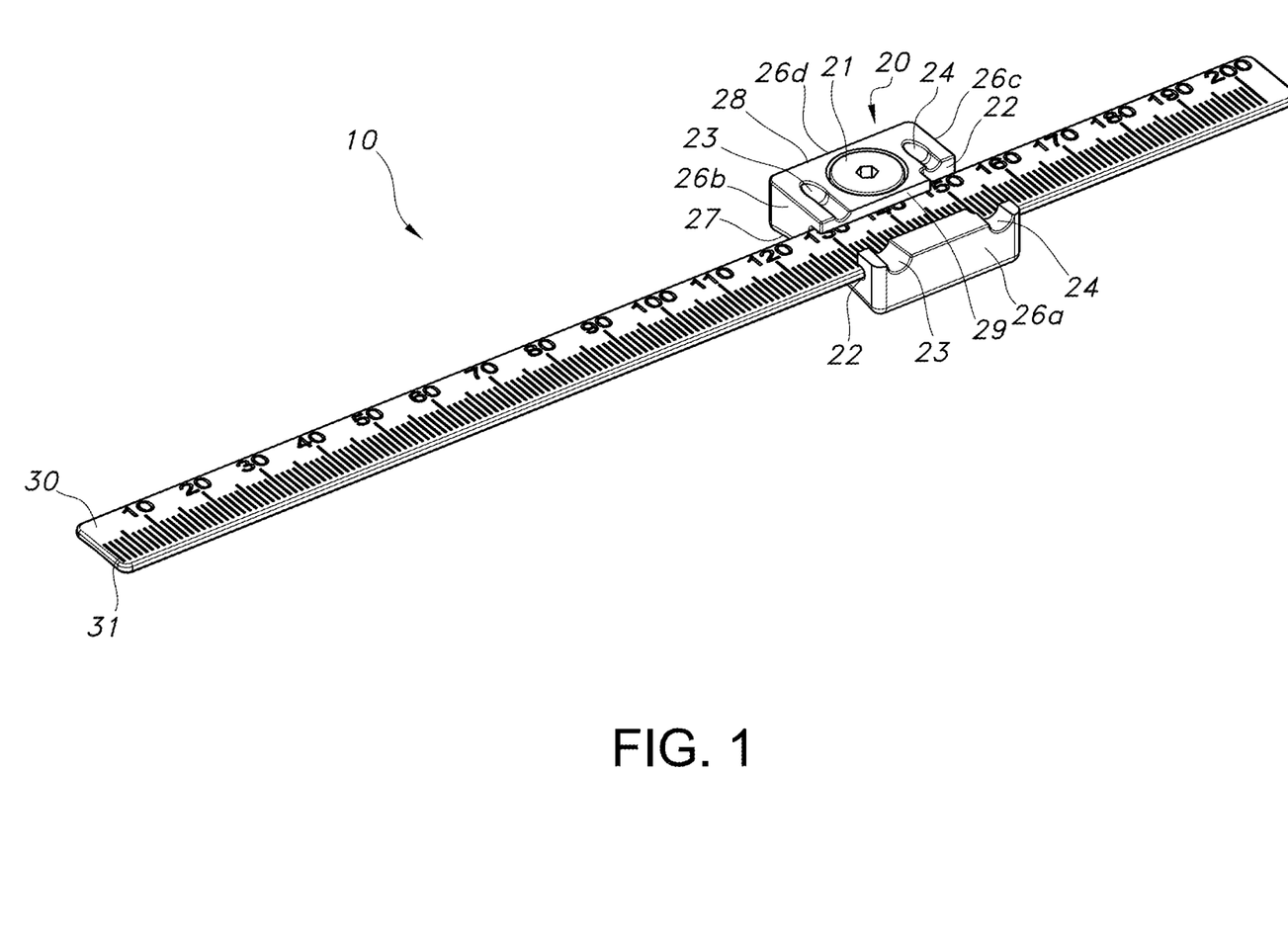
FIG. 1 illustrates an embodiment of a reference guide.

Referring to the figures wherein like numerals indicate like elements throughout the various figures, FIG. 1 shows a reference guide 10. Reference guide 10 may be used during surgery to identify a reference point with respect to a fixed point and can function independently of anatomical landmarks, which may become damaged or destroyed during a procedure. Thus, reference guide 10 can be useful when preparing a damaged bone, such as, for example, when performing a replacement arthroplasty on a damaged hip.

Reference guide 10 comprises a bone attachment portion 20 and a reference indicator 30. The bone attachment portion 20 illustrated in FIG. 1 is configured to attach to an unprepared surface of a bone. In other embodiments, the bone attachment portion 20 can be configured to attach to other items. The bone attachment portion 20 comprises a bone abutment surface 27 that is configured to mate with the surface of a bone. In one embodiment, the bone abutment surface 27 may have a concave surface designed to rest on a generally convex surface of a bone such as, for example, along the exterior surface of a femur. In other embodiments, it will be appreciated that the bone abutment surface 27 could have alternative profiles designed for mating with different anatomical structures. By way only of example, the bone abutment surface 27 could be convex, flat, pointed, contoured, or otherwise adaptively formed. In the embodiment of FIG. 1, by having a curved surface designed to generally compliment the surface of the bone to which the bone attachment portion 20 will be secured, a more secure base is established for the reference guide 10. According to some embodiments, the bone attachment portion 20 may comprise flexible or malleable material along the bone abutment surface 27 in order to allow the bone attachment portion 20 to better mate with the geometry of the bone or other structure to which it will attach. In other embodiments, a separate flexible or malleable material may be placed between the bone attachment portion 20 and the bone to better conform the bone attachment portion 20 to the underlying bone.

The bone abutment surface 27 can thus allow the reference guide 10 to be placed directly (or indirectly) on the surface of an unprepared bone and be rigidly and removably attached thereto as explained further below. In certain embodiments, the bone attachment portion 20 may be configured to attach to other tissue or structures in close proximity to a bone involved in a procedure in order to provide a reference point with respect to the bone involved in the procedure or other structure in close proximity to the reference guide.

Extending upwardly from the bone abutment surface 27 are sidewalls 26a-d, as shown in FIG. 1. Depending on the shape of the bone attachment portion 20, the number of sidewalls may vary. For example, if the bone attachment portion 20 is generally round, there may be only a single sidewall. If it is rectangular, then there may be four sidewalls. The sidewalls 26a-d shown in FIG. 1 are generally flat and perpendicular to the bone abutment surface 27 but in other embodiments, the sidewalls may form an oblique angle with the bone abutment surface 27 or may be curved. Moreover, the geometry of one or more of the sidewalls 26a-d may be different.

A top surface 28 connects the sidewalls 26a-d of the bone attachment portion 20. Top surface 28 is shown in FIG. 1 as being perpendicular to sidewalls 26a-d and generally planar and rectangular. Of course, in other embodiments, other configurations are possible. For example, the top surface 28 may be any suitable shape to connect with sidewalls 26a-d and may be oriented at an acute, obtuse, or any suitable oblique angle relative to sidewalls 26a-d, or be formed integrally with sidewalls 26a-d such that there is a smooth transition between the sidewalls 26a-d and top surface 28.

As shown in the embodiment of FIG. 1, fixation features 23, 24 are formed in the top surface 28 of the bone attachment portion 20. The fixation features 23, 24 shown in the embodiment of FIG. 1 comprise grooves that extend at least partially across the top surface 28 for receiving an attachment aid, such as cerclage cable or wire. In one embodiment, cerclage cable can be positioned into the fixation features 23, 24 and threaded through holes (not visible in FIG. 1) on the back sidewall 26d. Such holes in the back sidewall 26d may extend from an end of the fixation features 23, 24 through the bone attachment portion 20 and out the back sidewall 26d such that the cerclage cable can be fed from the fixation features 23, 24 through the holes and wrapped around a bone abutting the bone attachment portion 20. In another embodiment, the fixation features 23, 24 extend across the entirely of the top surface 28. Cerclage cable can then simply be positioned in the fixation features 23, 24 and wrapped around the bone. Generally speaking, the fixation features 23, 24 serve to allow a bone attachment aid (such as cable) to secure the bone attachment portion 20 to the bone. In other embodiments, fixation features 23, 24 may be holes or other suitable structures configured to receive a bone screw, wire, pin, bone spike, or other suitable bone attachment aid for securely fixing the reference guide 10 to a bone or other structure in a removable manner. In embodiments configured for use with cable or wire, a swagging member to assist with cable swagging can also comprise part of the bone attachment portion 20. In embodiments in which grooves or holes are provided for cerclage cable or wire or other suitable securing devices, the grooves or holes may be transversely, axially, or obliquely located relative to the longitudinal axis of the reference guide 10.

In embodiments using cabling to secure the reference guide 10 to a bone, the device can further function as a prophylactic cabling device to assist with reaming and stem removal to prevent or limit bone damage. For example, a surgeon or other user can attach the bone attachment portion 20 to the surface of a bone and secure it in place with cerclage cable threaded into fixation features 23, 24. The surgeon or other user can then prepare the bone by, for example, removing an existing implant component, or reaming or resecting a portion of the bone. The cerclage cable in place around the bone and bone attachment portion 20 can provide pressure to prevent splitting or other damage to the bone prior to or during reaming, resecting, or implant removal.

Figure 3:
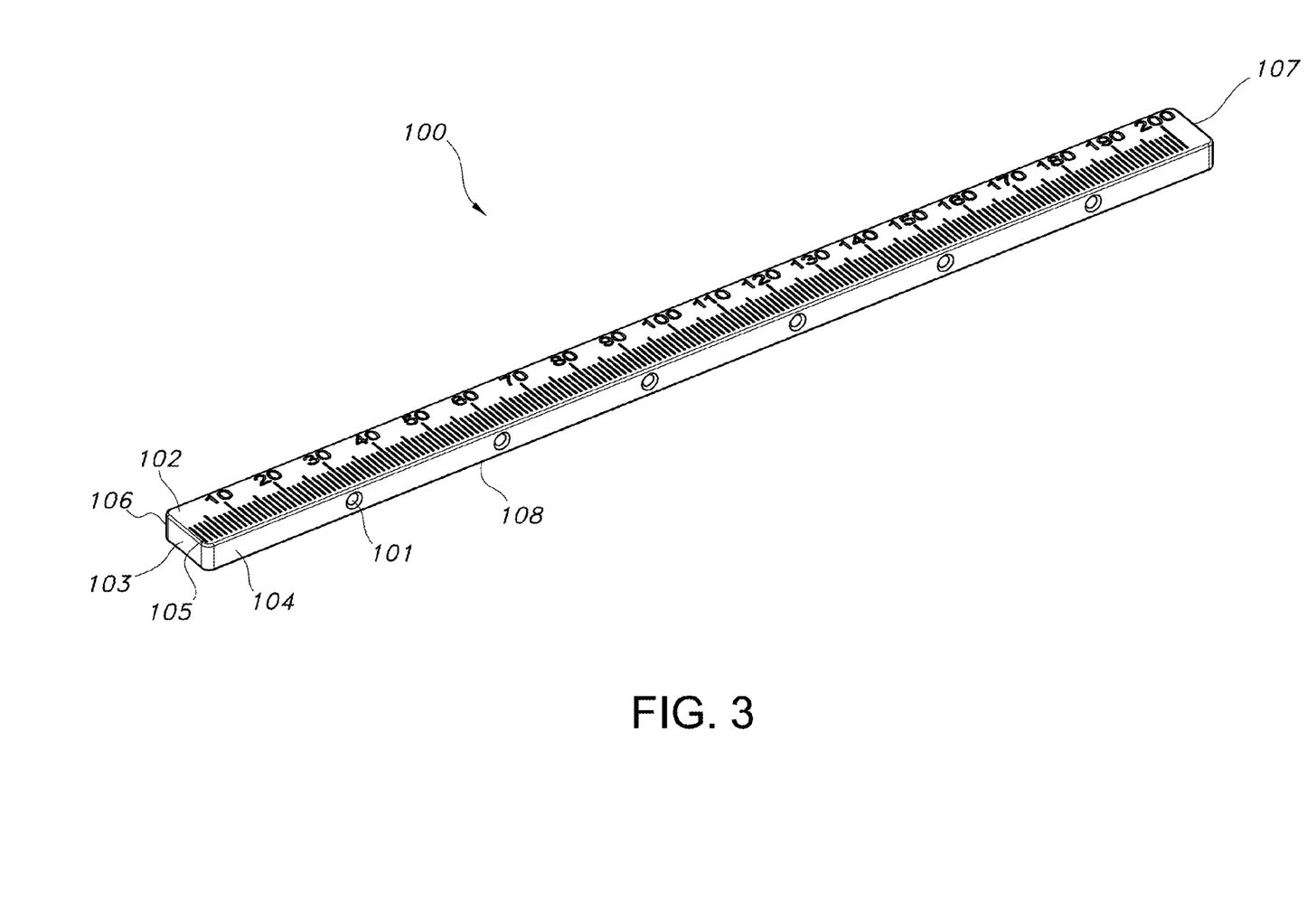
FIG. 3 illustrates another embodiment of a reference guide.

The bone attachment portion 20 shown in FIG. 1 further comprises a receiving channel 22 for a reference guide. Receiving channel 22 allows a reference guide, such as reference indicator 30 shown in FIG. 1, to couple with the bone attachment portion 20 in an adjustable and optionally removable manner. In other embodiments, it will be appreciated that the reference indicator 30 could be formed integrally with bone attachment portion 20 as shown in FIG. 3 and discussed further below. Receiving channel 22 receives reference indicator 30 in a sliding relationship. Receiving channel 22 may receive reference indicator 30 in a dovetailed or similar manner such that reference indicator 30 is restricted to translational movement within the receiving channel 22. In one embodiment, the bone attachment portion 20 includes a lip 29 that extends at least partially over the receiving channel 22 on either side of a top opening of the receiving channel 22 to prevent the reference indicator 30 from moving upwardly and disengaging from the receiving channel 22. Lateral movement perpendicular to the longitudinal axis of reference indicator 30 is prevented by a generally snug fit between the receiving channel 22 and the reference indicator 30 achieved by having the receiving channel 22 width being the same or only slightly larger than the width of the reference indicator 30.

The bone attachment portion 20 shown in FIG. 1 further includes a locking mechanism 21 for locking the reference indicator 30 in a fixed position with respect to bone attachment portion 20. In the embodiment shown in FIG. 1, locking mechanism 21 may be tightened in order to secure reference indicator 30 to the bone attachment portion 20. In the embodiment shown in FIG. 1, a tool may be used to engage the hex socket of locking mechanism 21 in order to turn it. When rotated, locking mechanism 21 may cause an external threaded portion of the locking mechanism 21 (not visible in FIG. 1) to engage a complimentary internal threaded portion (also not visible) and thus clamp the bone attachment portion 20 against the reference indicator 30. Alternatively, locking mechanism 21 may act by deforming the receiving channel 22 to create a press fit with reference indicator 30, by directly engaging reference indicator 30, or by other suitable techniques (e.g., the use of a ball detent or a set screw) that allow reference indicator 30 to be selectively and securely held in place within receiving channel 22. According to certain embodiments, locking mechanism 21 may include structure to positively lock reference indicator 30 in a single position and orientation with respect to bone attachment portion 20 such that it can be easily removed and returned to the same location.

Reference indicator 30, according to the embodiment shown in FIG. 1, is generally rectangular in shape and resembles a ruler. For example, reference indicator 30 can include reference marks 31 indicating a distance from one end of the reference guide along the length of the guide. When secured with respect to the bone attachment portion 20, which in turn is secured by bone connection aids, such as cerclage cable placed in fixation features 23 and 24, the reference marks 31 can identify fixed reference points with respect to a longitudinal axis of the underlying bone and can thus indicate, for example, an axial depth reference for reaming a bone or a desired axial location of a head center for a new implant. Such reference points can be useful when other anatomical reference points may be missing or could be sacrificed during the impending procedure.

For example, when performing a replacement hip arthroplasty, portions of the femoral head or greater or lesser trochanter may already be missing or may be damaged or otherwise compromised during removal of the existing implant. In such circumstances, reference guide 10 may be used (and more specifically reference marks 31 on reference indicator 30) to provide needed reference points. More particularly, a surgeon may determine a desired reamer depth or axial location of a new implant head center preoperatively with respect to either the existing implant or existing anatomical reference points. Then, intraoperatively, the surgeon can attach the reference guide 10 to provide a fixed reference frame for the surgical site. After attaching the reference guide 10, a surgeon can note where the desired location that was determined based on existing landmarks or an existing implant aligns with respect to the reference guide. Because the reference guide provides a stable reference system that will not be compromised as the existing implant is removed, a surgeon can now proceed to remove the existing reference frame without fear of losing needed landmarks for placement of the new component.

According to certain embodiments, reference indicator 30 may be capable of being shaped during surgery in order to conform to anatomy or to avoid obstacles in the surgical field such as other reference guides attached to the surgical site. For example, the reference indicator 30 may be made of a malleable material, that with directed and intentional force can be conformed to follow the shape of a bone. The reference guide may also be conformed to avoid constraints imposed by surgical equipment. For example, the reference guide may by molded to bend around a portion of the surgical site in order to provide clearance for a resecting or reaming device. In embodiment using a malleable reference guide, the guide may still resist deformation due to sudden inadvertent force. In this manner the guide can be optimally positioned and still function as a fixed reference frame relative to the bone attachment portion 20.

Reference guide 10 thus provides a device that can be attached to an unprepared surface of a bone and that provides a fixed and easily identifiable reference frame for a surgical site. Once the bone abutment portion 20 is fixed with respect to an anatomical feature, such as the bone it abuts, and the position of the reference indicator 30 is identified with respect to the bone abutment portion 20, the reference guide 10 provides a reference frame that can be used to identify or confirm desired locations in the surgical site without relying on other landmarks that may be compromised. Additionally, because reference guide 10 can attach to wide range of bones or other anatomical structures and because reference indicator 30 can provide an adjustable reference frame with respect to an arbitrary attachment point, reference guide 10 can attach to an unprepared bone surface. For example, it is not necessary to shape, mark, drill, or otherwise prepare a bone surface in order for reference guide 10 to provide reference points for a surgeon as is explained more fully below.

Figure 2:
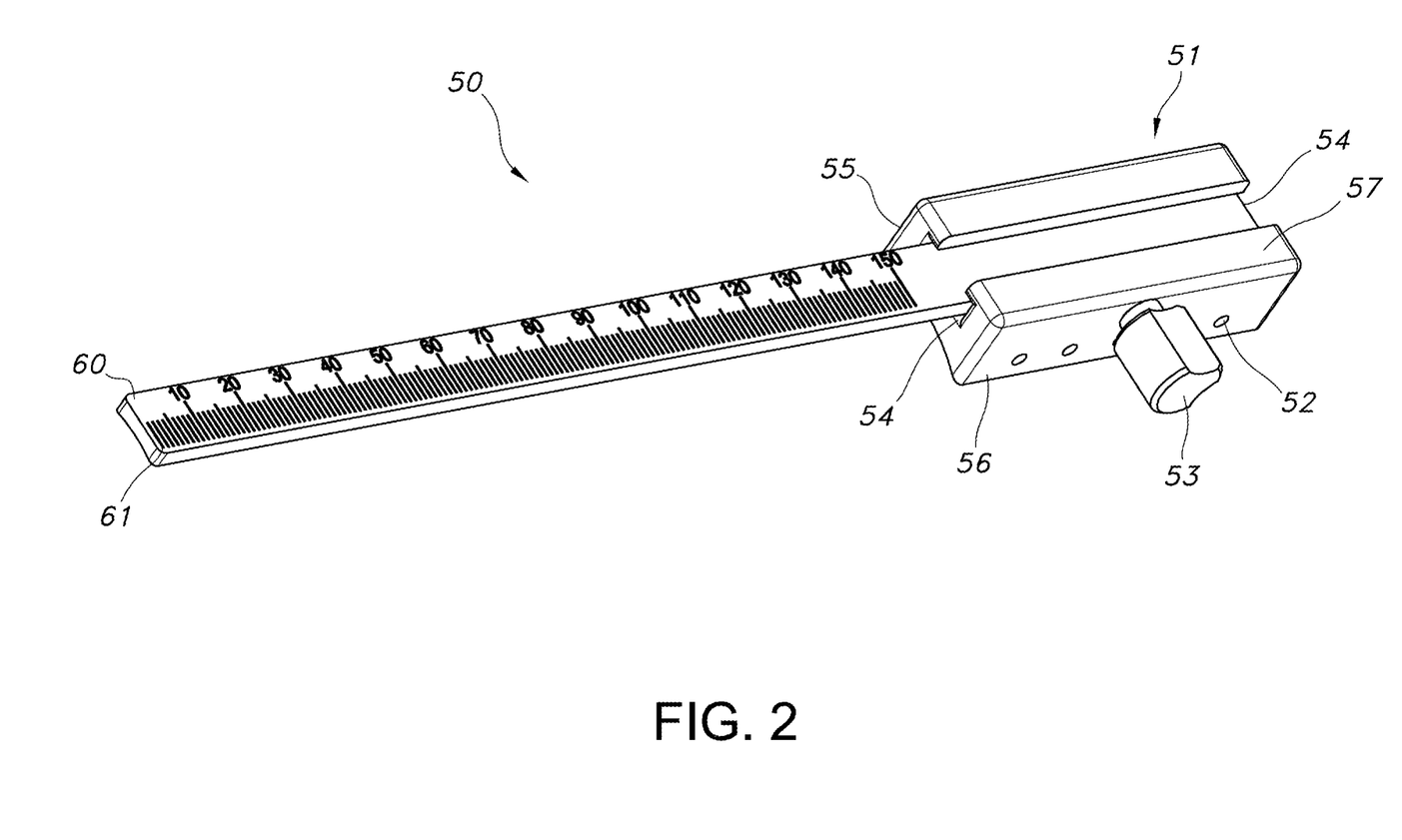
FIG. 2 illustrates an alternative embodiment of a reference guide.

FIG. 2 illustrates an alternate embodiment of a reference guide. Reference guide 50 shown in FIG. 2 comprises bone attachment portion 51 and a reference indicator 60 having reference marks 61. Bone attachment portion 51 shown in FIG. 2 is similar to bone attachment portion 20 shown in FIG. 1, but in place of grooves for receiving cerclage cable, bone attachment portion 51 comprises fixation features 52 in a front sidewall surface 56 that extend through the bone attachment portion 51 and out through a back sidewall 55 for receiving cerclage cable. Fixation features 52 may comprise openings that extend through the bone attachment portion 51 underneath receiving channel 54, or, in other embodiments, may form grooves across an upper surface 57 of bone attachment portion 51. Locking mechanism 53 shown in FIG. 2 resembles locking mechanism 21 from FIG. 1, but as shown in FIG. 2, comprises a knob that may be twisted to engage a threaded member (not shown) against a portion of reference indicator 60 within receiving channel 54. As seen in FIG. 2, reference marks 61 need not extend the entire length of reference indicator 60.

FIG. 3 illustrates yet another alternative embodiment for a reference guide. In reference guide 100, the bone attachment portion and reference indicator are formed integrally as part of a single unit having a front sidewall 104, a back sidewall 106, and two end sidewalls 103, 107. Fixation apertures 101 extend through the reference guide 100 between the front sidewall 104 and the back sidewall 106. A top surface 102 connects the front sidewall 104, back sidewall 106, and end sidewalls 103, 107 and includes reference indicators 105. The sidewalls extend down from the top surface 102 to connect with a bottom bone abutment surface 108. The bone abutment surface 108 may be contoured as described above, or may be generally flat. In the embodiment shown in FIG. 3, the bone abutment surface 108 is generally flat. A single integral unit, such as the embodiment shown in FIG. 3, may be manufactured from relatively inexpensive material and thus may be suitable for single disposable use. Additionally, a single integral unit may be made of bio-compatible or bio-resorbable material suitable for implantation in the body.

Figure 4:
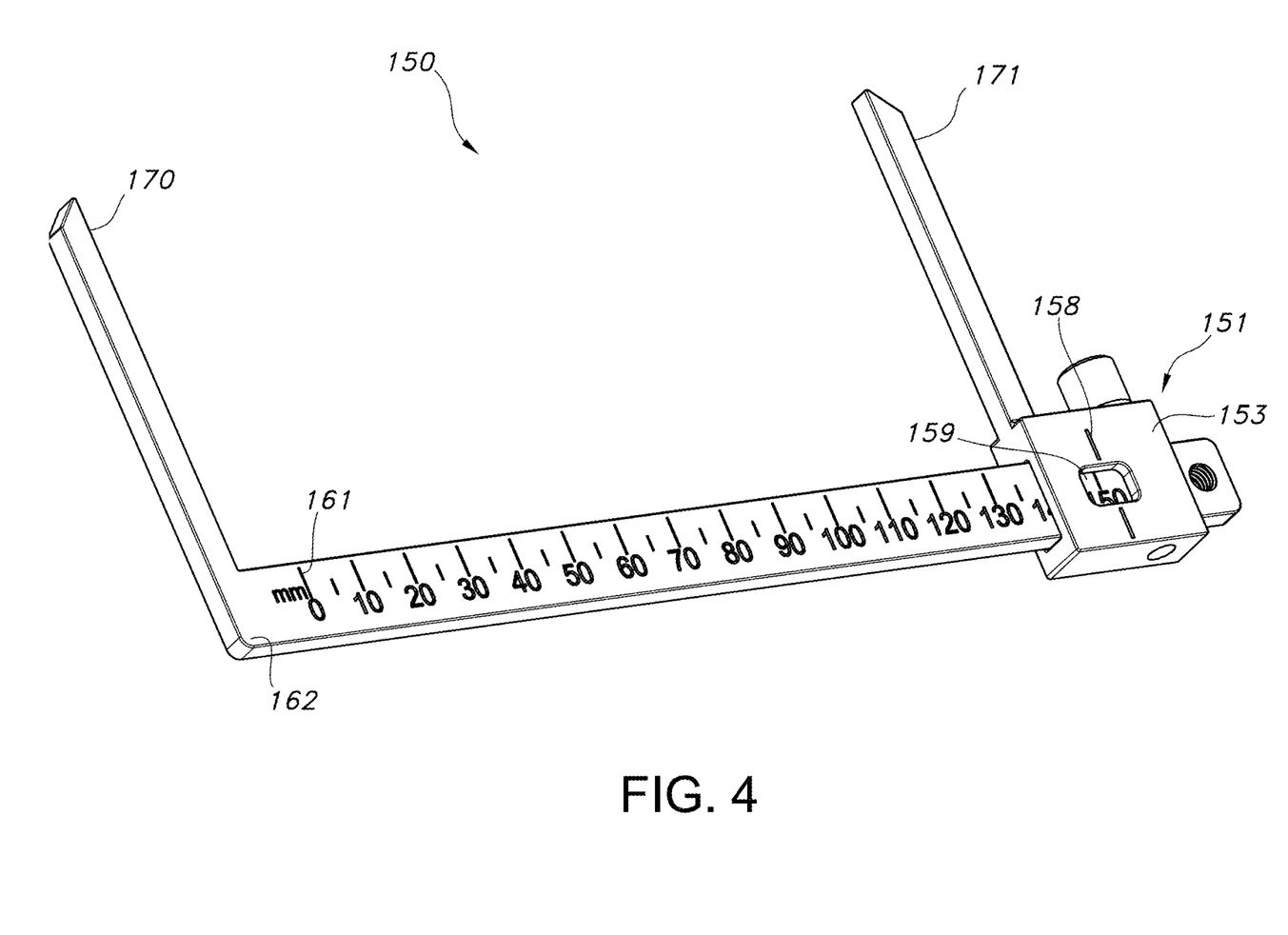
FIG. 4 illustrates yet another embodiment of a reference guide.

FIG. 4 illustrates still another embodiment of a reference guide. The reference guide 150 illustrated in FIG. 4 comprises a bone attachment portion 151 and a reference indicator 162. Extending in a direction generally perpendicular to the longitudinal axis of reference indicator 162 are reference extensions 170 and 171. Reference extensions 170 and 171 can facilitate alignment of a desired location or landmark with the reference indicator 162, such as for example, when the desired location or landmark is not generally coaxial with the reference indicator 162. According to the embodiment illustrated in FIG. 4, one reference extension 170 is formed integral with the reference indicator 162 such that it remains in a fixed position with respect to reference indicator 162. The second reference extension 171 is formed integral with the bone attachment portion 151 and thus remains in a fixed position with respect to the bone attachment portion 151. While the embodiment shown in FIG. 4 comprises integrally formed reference extensions 170, 171, reference extensions 170, 171 may alternatively be removably attached to the reference guide 150. The reference extensions may be of varying length or have an adjustable length. For example, in the embodiment of a reference guide 200 illustrated in FIG. 5, the reference extensions 220, 221 may be relatively short as compared to the reference extensions 170, 171 of the reference guide 150.

Figure 5:
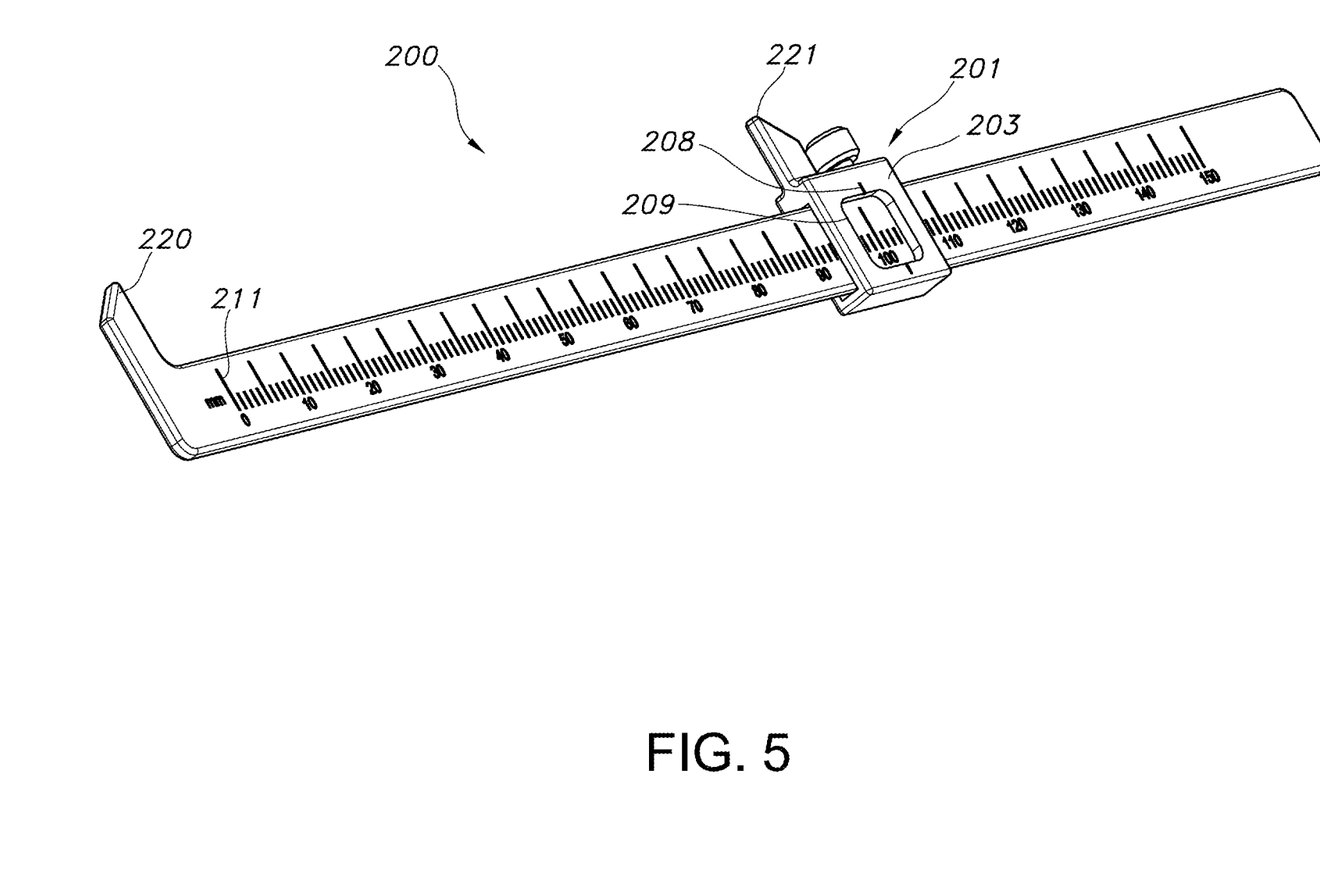
FIG. 5 illustrates still another embodiment of a reference guide.

The bone attachment portions 151 illustrated in FIGS. 4, and 201 in FIG. 5, resemble the bone attachment portion 20 illustrated in FIG. 1 in general function, but demonstrate additional possible design alternatives consistent with various embodiments of the invention. For example, the bone attachment portions 151 and 201 comprise reference openings 159 and 209 respectively, configured to allow a user to view reference marks 161 or 211 through a top surface 153 or 203 and to gauge alignment with a second reference mark 158 or 208 on the top surface 153 or 203 of the bone attachment portion 151 or 201.

Figure 6:
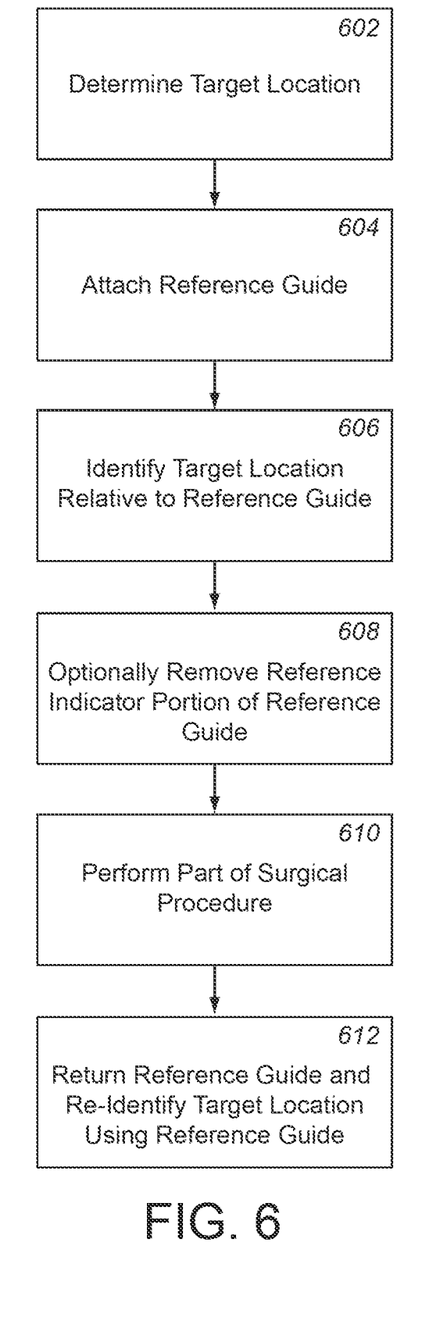
FIG. 6 illustrates an embodiment of a method for using a reference guide in a surgical procedure.

The reference guides described above may be used in a variety of surgical methods. FIG. 6 illustrates one embodiment of a method 600 for using a bone preparation reference guide. The example method shown in FIG. 6 may be used, for example, when determining a reference location for femoral preparation for a revision hip arthroplasty. While the method 600 shown in FIG. 6 is described with respect to performing a revision hip arthroplasty, embodiments of method 600 encompass other procedures as well. The description of a revision hip arthroplasty is simply to facilitate a description of the method 600 and does not limit the method 600 to a particular surgical procedure.

The method 600 shown in FIG. 6 begins in block 602, wherein a surgeon can first determine a desired target location. The target location may be, for example, a desired axial location of a head center, or other suitable reference point, for a new implant and may be based on current anatomical landmarks such as a greater or lesser trochanter or on a landmark from a previous implant, such as a head center from the current implant. Alternatively, the target location may be another suitable location relevant to the surgical procedure such as a reamer depth or a resection line. The target location may be identified preoperatively with the aid of x-rays or other imaging technology, or during the operation by other suitable techniques.

After block 602, the embodiment of method 600 shown in FIG. 6 moves to block 604, where a reference guide, such as reference guide 10 shown in FIG. 1, is attached to an unprepared bone surface at a location distal to any previous or planned osteotomies. For ease of discussion, an embodiment of the method will be discussed using reference guide 10. However, one of skill in the art will readily understand that any of the reference guides discussed herein may be used. The reference guide 10 can then be removably secured to the unprepared bone using bone attachment aids such as a cerclage cable, wire, or bone screws. In embodiments using a device as shown in FIG. 1, removably securing the reference guide to the unprepared bone surface can comprise first securing the bone attachment portion 20 and then inserting reference indicator 30 into receiving channel 22. In embodiments using a device as shown, for example, in FIG. 3, wherein the reference indicator is formed integral with the bone attachment portion, the reference guide 10 may be attached to the bone as a single action without requiring a separate placement of the reference indicator within the receiving channel of the bone attachment portion.

Once the reference guide 10 is attached to the unprepared bone distal to any previous or planned osteotomies, the method 600 shown in FIG. 6 proceeds to block 606, wherein a surgeon or other user uses the reference indicator 30 to identify the desired target location for the procedure with respect to the reference guide. For example, if the target location is the axial location of the new implant head center, this position may be marked by noting where the existing head center aligns with the reference indicator 30, and marking that location to identify the center location for the new implant head center. According to some embodiments, identifying the desired target location with respect to the reference indicator 30 may involve referencing reference marks 31 that indicate a distance from the bone attachment portion 20 of the reference guide, along a longitudinal axis of the guide, to the desired target location. For example, a surgeon or other user may determine that the target location for the implant head center (based on the location of the existing head center or other suitable pre-operative measurements) is a given number of centimeters from the bone attachment portion 20. This can be done by simply marking with which reference mark 31 an existing implant head center aligns and noting that as the location for the future implant head center. In other embodiments, a surgeon may adjust the position of the reference indicator 30 to clearly identify a desired target location. For example, a surgeon may palpate in an area near the greater trochanter in order to identify the precise location of the greater trochanter and then adjust the reference indicator 30 such that a tip of the reference indicator 30 aligns with the location of the greater trochanter. The reference indicator 30 can then be fixed in this position and used, for example, to guide a reaming depth. Having an easily discernable and fixed reference point can provide greater accuracy than relying on an anatomical reference point such as a greater trochanter, which due to overlying soft tissue may be less discernable and reliable as a reference mark for aligning a reaming device while reaming.

According to certain embodiments, a surgeon may use a skin pen or other marking instrument to mark the reference indicator 30 with a reference point corresponding to the target location. For example, a surgeon may determine where the existing implant or other relevant landmark aligns with the reference guide and then mark that location. In other embodiments, a surgeon may slide the reference indicator 30 within receiving channel 22 such that a selected reference mark 31 aligns with the target location. Once a reference is established for a desired location, such as by establishing a distance from the bone attachment portion 20 to the desired location for the new implant head center, or marking where on the reference indicator 30 an existing head center aligns, a surgeon or other user may optionally remove the reference indicator 30 from the bone attachment portion 20 as indicated in block 608. Prior to removing the reference indicator 30, a surgeon can note not only where the target location aligns with respect to reference indicator 30, but also where reference indicator 30 aligns with the bone attachment portion 20. For example, a surgeon can note where an edge of sidewall 26b or other suitable portion of the bone attachment portion 20 aligns with the reference indicator 30 so that it can be returned to the same location and orientation with respect to the bone attachment portion 20. Removing the reference indicator 30 may allow better access to the surgical site for removal of an existing implant for example.

Once a desired location is identified with respect to the reference guide, the method 600 shown in FIG. 6 proceeds to block 610, wherein a surgeon or other user proceeds with the surgical procedure such as by removing an existing stem from the bone. Note that during this procedure certain bony or other landmarks may be damaged or destroyed. However, because the reference indicator 30 can be reattached to the bone attachment portion 20, and because the target location (such as the desired placement of the new implant component) is known with respect to the reference indicator 30, the loss of bony landmarks or landmarks of the existing implant does not hamper the procedure. For example, even if existing bony landmarks break during removal of the stem, and after the stem is no longer in place, a proper alignment of the new implant head center can be easily determined by reattaching reference indicator 30 and noting the previously marked target location with respect to reference indicator 30.

Thus, as indicated in block 612, the surgeon may proceed with the operation by referencing the reference guide 10 to identify the target location and proceed to complete the surgical procedure using the correct location. (In embodiments in which the reference indicator 30 was removed from the bone attachment portion, it is of course replaced prior to determining the target location). For example, in a revision arthroplasty, a surgeon may replace the reference indicator 30, align a mark on a reaming or broaching device with a reference mark on the reference indicator to confirm the target location of a reaming depth, and proceed to ream the bone to that depth, even in the absence of traditional landmarks.

According to certain embodiments, the reference guide may be made from relatively inexpensive material intended for a single disposable use such as plastics, ceramics, or metal. According to other embodiments, the reference guide may be made of bio-compatible and bio-resorbable material such that the device can be implanted in a patient. The resorbable materials may include polymeric materials, such as poly-alpha-hydroxy acids, polylactide and polyglycolide, including their copolymers. The use of slow degrading and highly crystalline polymers or fast-degrading copolymers is envisioned as is the use of injectable or crosslinkable polymers, including, but not limited to, photopolymerizable and chemically polymerizable polymers and polymers that harden in situ. Resorbable materials for use in the devices according to the embodiments of the present invention are not limited to the foregoing and includes any fully or partially degradable or erodible in a body chemical composition or material suitable for use in the devices according to the embodiments of the present invention, including but not limited to carbohydrates and derivatives thereof, such as such as cellulose or hyaluronic acid, in resorbable devices of various embodiments.

Various embodiments of the invention have been described in fulfillment of the various objectives of the invention. It should be recognized that these embodiments are merely illustrative of the principles of the present invention. Numerous modifications and adaptations thereof will be readily apparent to those of skill in the art without departing from the spirit and scope of the invention.

We claim:

1. A method for determining a reference point for a surgical procedure, the method comprising:
   determining a target location for a surgical procedure;
   providing a reference guide comprising an abutment surface configured to abut an unprepared surface of a bone;
   attaching the reference guide to the bone such that the abutment surface abuts the unprepared surface of the bone, wherein the attaching the reference guide to the bone comprises securely fixing the reference guide to the bone in a fixed position using a bone attachment aid;
   identifying a reference position on the reference guide that corresponds to the target location; and
   completing a surgical procedure based at least in part on referencing the reference position on the reference guide.

2. The method of claim 1, wherein the target location is along a longitudinal axis of the bone to which the reference guide is attached.

3. The method of claim 1, wherein the identifying a reference position on the reference guide comprises measuring a distance to the target location.

4. The method of claim 1, wherein the identifying a reference position on the reference guide comprises identifying a reference mark on the reference guide.

5. The method of claim 1, wherein the attaching the reference guide to the bone comprises positioning a cable around the reference guide and the bone.

6. The method of claim 1, wherein the attaching the reference guide to the bone comprises feeding a cable through at least a portion of the reference guide and wrapping the cable around the bone.

7. The method of claim 1, wherein the providing a reference guide further comprises providing a reference indicator and a bone attachment portion comprising the abutment surface and positioning the reference indicator within a channel in the bone attachment portion.

8. The method of claim 7, wherein the attaching the reference guide to the bone comprises attaching the bone attachment portion to the bone such that the abutment surface abuts the unprepared surface of the bone.

9. The method of claim 7, further comprising locking the reference indicator in a position relative to the bone attachment portion.

10. The method of claim 7, wherein the identifying a reference position on the reference guide that corresponds to the target location comprises identifying the reference position on the reference indicator.

11. The method of claim 10, further comprising removing the reference indicator from the channel of the bone attachment portion, performing a portion of the surgical procedure that alters or eliminates at least one surgical landmark, and re-positioning the reference indicator in the channel of the bone attachment portion in order to re-identify the target location without the use of the landmark by referencing the reference position on the reference indicator.

12. The method of claim 7, further comprising:
    sliding the reference indicator within the channel in the bone attachment portion to a select position; and
    securing the reference indicator in the select position relative to the bone attachment portion using a locking mechanism.

13. The method of claim 12, wherein the locking mechanism comprises at least one of a set screw, ball detent, and a press fit connection.

14. The method of claim 7, further comprising sliding the reference indicator within the channel in the bone attachment portion; and
    wherein the sliding of the reference indicator within the channel is restricted to translational movement generally parallel to a longitudinal axis of the reference indicator.

15. The method of claim 7, wherein the reference indicator extends along a longitudinal axis, and wherein the reference indicator includes reference markings spaced apart from one another along the longitudinal axis.

16. The method of claim 7, wherein the reference indicator extends along a longitudinal axis; and
    wherein the longitudinal axis of the reference indicator is positioned generally along a central axis of the bone when the abutment surface of the bone attachment portion is positioned in abutment against the unprepared surface of the bone.

17. The method of claim 1, wherein the abutment surface of the reference guide comprises a contoured surface that substantially matches an outer contour of the unprepared surface of the bone.

18. The method of claim 17, wherein the attaching the reference guide to the bone comprises abutting the contoured surface of the reference guide against the outer contour of the unprepared surface of the bone.

19. The method of claim 18, wherein the abutting comprises mating the contoured surface of the reference guide against the outer contour of the unprepared surface of the bone.

20. The method of claim 19, wherein the contoured surface of the reference guide is concave and the outer contour of the unprepared surface of the bone is convex.

21. The method of claim 1, wherein the abutment surface of the reference guide comprises a concave surface sized and shaped for abutment against a corresponding convex surface of the unprepared surface of the bone.

22. The method of claim 1, wherein the abutment surface of the reference guide comprises a malleable material; and
   wherein the attaching of the reference guide to the bone comprises conforming the malleable material of the abutment surface to the unprepared surface of the bone.

23. A method for determining a reference point for a surgical procedure, the method comprising:
   determining a target location for a surgical procedure;
   providing a reference guide comprising an abutment surface configured to abut an unprepared surface of a bone;
   attaching the reference guide to the bone such that the abutment surface abuts the unprepared surface of the bone, wherein the attaching the reference guide to the bone comprises connecting a flexible member to the reference guide and engaging the flexible member with the bone;
   identifying a reference position on the reference guide that corresponds to the target location; and
   completing a surgical procedure based at least in part on referencing the reference position on the reference guide.

24. The method of claim 23, wherein the flexible member comprises a cable or wire.

25. The method of claim 23, wherein the engaging the flexible member with the bone comprises wrapping the flexible member around the bone.

26. The method of claim 23, wherein the connecting the flexible member to the reference guide comprises feeding the flexible member through an aperture in the reference guide.

27. The method of claim 26, wherein the aperture in the reference guide comprises a channel opening onto and extending at least partially across a top surface of the reference guide opposite the abutment surface.

28. The method of claim 27, wherein the channel opens onto a side surface of the reference guide extending between abutment surface and the top surface.

29. The method of claim 23, wherein the attaching the reference guide to the bone comprises connecting a pair of the flexible members to the reference guide and wrapping the pair of flexible members about the bone.

\* \* \* \* \*